United States Patent [19]

Dawson

[11] 4,417,581

[45] Nov. 29, 1983

[54] CORNEAL ELECTRODE FOR ELECTRORETINOGRAPHY

[75] Inventor: William W. Dawson, Gainesville, Fla.

[73] Assignee: The University of Florida, Gainesville, Fla.

[21] Appl. No.: 194,936

[22] Filed: Oct. 7, 1980

Related U.S. Application Data

[63] Continuation of Ser. No. 41,777, May 23, 1979, abandoned.

[51] Int. Cl.³ .............................................. A61B 5/04
[52] U.S. Cl. .................................... 128/639; 128/642; 128/734
[58] Field of Search ................................ 128/639-644, 128/783, 784, 793, 798, 802, 803, 419 P, 734

[56] References Cited

U.S. PATENT DOCUMENTS

| 3,137,291 | 6/1964 | Phipps | 128/639 |
| 3,542,010 | 11/1970 | Love | 128/644 |
| 4,102,331 | 7/1978 | Grayzel et al. | 128/640 |

FOREIGN PATENT DOCUMENTS

| 122258 | 2/1972 | Denmark | 128/639 |
| 1219017 | 1/1971 | United Kingdom | 128/419 P |

OTHER PUBLICATIONS

Shaw, "A Wire Multielectrode for Intramuscular Recording," Med. & Biol. Eng., Sep. 1974, pp. 721-723.

Primary Examiner—Lee S. Cohen
Attorney, Agent, or Firm—Arthur G. Yeager

[57] ABSTRACT

Corneal electrode comprising an electrically conductive metal wire conductively attached to a yarn of silver-coated nylon fibers. This electrode is employed to measure the change in an electric potential when the eye is subjected to light.

10 Claims, 2 Drawing Figures

CORNEAL ELECTRODE FOR ELECTRORETINOGRAPHY

This is a continuation of application Ser. No. 041,777, filed May 23, 1979, now abandoned.

BACKGROUND OF THE INVENTION

Considerable research has been undertaken for many years to understand how the human eye functions when receiving light and transmitting signals concerning that light to the brain. One of the areas of research has been in electroretinography, which is a study of the electrical potentials produced in the eye. It can be readily understood that because of the extreme sensitivity of the eye these measurements are difficult to obtain. Furthermore the results may be confused by potentials which are due to muscular activity, pain reflexes, etc. A general survey of the types of electrodes and procedures which have been used in the past may be found in the article by Riggs entitled "Electrophysiological Technique for Studying Visual Function in Man: A Historical Overview", J. Opt. Soc. Amer. 67, 1451-7(1977). As this article will show the most common procedure is to employ any of several types of contact lenses which are fashioned with a built in electrode lead which can be connected to a suitable device for the measurement of the potential. Each of the known contact lens electrode devices suffers from one or more of the following disadvantages:

(1) The electrode and contact lens assembly is large and frightens children.
(2) The contact lens distorts the optics of the eye.
(3) The electrode and/or the lens frequently scrapes the corneal epithelium.
(4) The electrode and contact lens assembly must be made in several specific sizes for different patients.
(5) The electrodes and contact lens assembly is expensive, is not disposable, and cannot be sterilized in an autoclave.
(6) The contact lens assembly can abrade conjunctival sac tissues.
(7) The contact lens assembly is often painful when in place.
(8) Anesthetic must be used.

It is an object of the present invention to provide a corneal electrode for use in electroretinography which does not suffer from these disadvantages and which is capable of measuring the potential with at least the same degree of accuracy as that of the best of the prior art contact lens systems.

The novel features believed to be characteristic of this invention as set forth with particularity in the appended claims. The invention, however, both as to its organization and method of operation, together with further objects and advantages thereof may best be understood by reference to the attached drawings and to the following description.

BRIEF SUMMARY OF THE INVENTION

This invention provides a corneal electrode for use in electroretinography comprising an electrically conductive metal wire conductively attached to a yarn of electrically conductive fibers, preferably silver-coated nylon fibers. In the specific embodiments of this invention the yarn comprises 3-6 individual fibers, the fibers are about 10-15 microns in diameter, and the yarn is attached to the metal wire by means of a conductive epoxy cement.

DETAILED DESCRIPTION OF THE INVENTION

Figure 1:
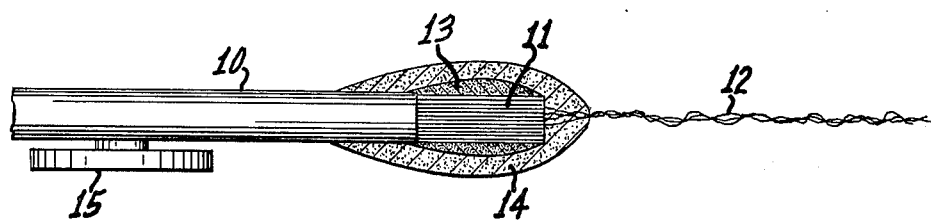
FIG. 1 is a schematic illustration of the electrode of this invention.

In FIG. 1 there is shown corneal electrode of this invention. An ordinary copper strand wire 10 preferably 24 gauge electronic "hook-up" wire, having vinyl or other comparable insulation is the lead wire of this device. A small terminal portion of wire 10 is stripped of its insulation leaving the bare strands of copper wire 11 to be attached to silver-coated fibers of nylon 12. Such silver-coated fibers of nylon are manufactured under the trade name "X-Static" by the Rohm and Haas Company of Philadelphia, Pa. These silver-coated fibers and their method of preparation are described in one or more of U.S. Pat. Nos. 3,792,520 to Weiner; 3,877,965 to Broadbent et al; and 4,042,737 to Forsgren et al. It is not critical that the conductive fibers of the electrode of this invention be silver-coated nylon fibers since other conductive metals can be employed, other types of fiber can be employed, and the conductive metal may be impregnated rather than coated on the fiber. Other metals include rhodium, gold, platinum, palladium, etc. Other types of fibers include polyester, acrylic, polyolefin, etc. Silver-coated nylon is preferred because of its ready availability, low mass, the high conductivity of silver, and the reasonable cost of the product.

The juncture between copper wires 11 and silver-coated nylon fibers 12 is made by interspersing the fibers individually among the several strands of wire to provide the best possible contact between the wires and the fibers, and then applying a conductive cement 13 to bind the wires to the fiber. Conductive epoxy cement is suitable for this purpose. When that cement has sufficiently dried and hardened the entire area is covered with a layer of rapid drying epoxy cement 14 which is nonconductive and thus can function as an insulator. This method of joining copper wire to silver-coated nylon fibers has proved to be entirely satisfactory and the resulting product is reasonably small in size. Support button 15 is attached about 1-2 cm from the epoxy-covered junction by cementing or any other suitable means. This button is used as a point of attachment to the skin of the patient to support the electrode in a fixed position.

Figure 2:
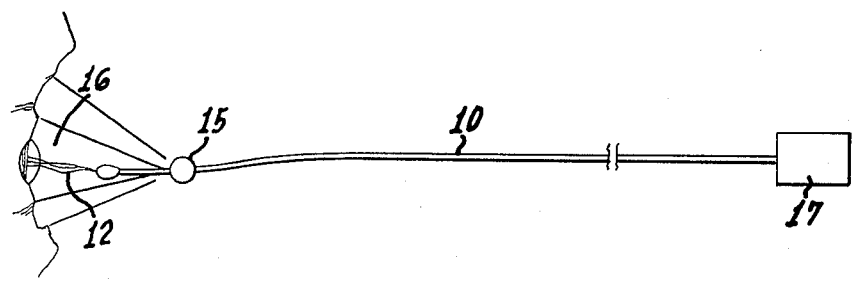
FIG. 2 is a schematic illustration of the electrode system of this invention and how it is used to measure potentials of the eye.

In FIG. 2 it may be seen how the electrode of this invention is employed. Support button 15 is attached to the skin of the patient near the outer can thus by a suitable adhesive. Silver-coated nylon fibers 12, which are approximately 2 cm in length are then available to be placed next to the eye 16. This is most easily accomplished by employing a small plastic or wire rod having a crook-shaped end portion. The crook is moistened with an artifical tear solution, and possibly with the addition of methyl cellulose, and this is touched to the silver-coated thread which then remains attached to the moistened crook by reason of surface tension. With the assistance of an optical loupe the thread can then be stretched across the cornea of the open eye. When the crook has been moved far enough it will release the moistened thread and permit it to drop onto the surface of the cornea where separate independent free ends of the fibers float on the surface film of the eye. In actual use the thread is not seen or felt by the patient. On occasion tears will wash the thread out of the eye and it must be replaced as described above.

In use the thread in position on the cornea measures potentials of the eye against a standard silver-silver chloride electrode attached to the skin adjacent the outer canthus and both electrodes are hooked up to a preamplifier. The ground site is a silver-silver chloride button attached to the center of the forehead with electrode paste. Lead wire 10 is attached, preferably through a preamplifier to a suitable electrical potential recording device 17. Actual measurements on patients employing both the device of this invention and the best contact lens electrode produced similar graphs. The electrode of this invention provide no discomfort to the patient and it was put into operation without an anesthetic or other medication. The electrode of this invention may be readily sterilized by the standard autoclave and the thread is sufficiently inexpensive that for most purposes it can be considered disposable.

While the invention has been described with respect to certain specific embodiments it will be appreciated that many modifications and changes may be made by those skilled in the art without departing from the spirit of the invention. It is intended, therefor, by the appended claims to cover all such modifications and changes as fall within the true spirit and scope of the invention.

What is claimed as new and what is desired to secure by Letters Patent of the United States is:

1. Corneal electrode for use in electroretinography comprising a yarn of electrically conductive fibers, means for electrically conductively attaching one end of said yarn to a device for measuring electrical potential, and the other end of said yarn comprising separate independent free ends of said fibers said free ends being unconnected to each other and of such dimension and material to permit contact with a surface film of a cornea without substantial abrasive effect thereon.

2. The electrode of claim 1 in which the electrically conductive fibers are silver-coated nylon fibers.

3. The electrode of claim 2 in which the yarn comprises 3-6 individual fibers.

4. The electrode of claim 2 in which each nylon fiber is about 10-15 microns in diameter.

5. The electrode of claim 1 in which said means for electrically conductively attaching is an electrically conductive metal wire which in turn is attachable to a device for measuring electrical potential.

6. A process for measuring electrical potentials produced in the eye which comprises contacting the surface film of the cornea with a yarn having substantially no abrasive effect on the eye and consisting essentially of electrically conductive fibers and measuring the electrical potential in the eye by means of an electrical potential measuring device conductively attached to said yarn through an electrical conductor.

7. The process of claim 6 wherein said fibers are silver-coated nylon fibers.

8. The process of claim 7 wherein said yarn comprises 3-6 individual fibers.

9. The process of claim 7 wherein each individual fiber is about 10-15 microns in diameter.

10. The process of claim 6 wherein said electrical conductor is attached to said yarn by electrically conductive epoxy cement.

* * * * *

UNITED STATES PATENT AND TRADEMARK OFFICE
CERTIFICATE OF CORRECTION

PATENT NO. : 4,417,581
DATED : November 29, 1983
INVENTOR(S) : William W. Dawson It is certified that error appears in the above-identified patent and that said Letters Patent are hereby corrected as shown below:

Col. 2, line 57, change "can thus" to read -- canthus --

Signed and Sealed this

Seventh Day of February 1984

[SEAL]

Attest:

GERALD J. MOSSINGHOFF

Attesting Officer          Commissioner of Patents and Trademarks